United States Patent
Willett et al.

(10) Patent No.: US 8,721,970 B2
(45) Date of Patent: May 13, 2014

(54) TEMPERATURE AND HUMIDITY COMPENSATED SINGLE ELEMENT PELLISTOR

(75) Inventors: Martin Willett, Waterlooville (GB); Martin Jones, Havant (GB)

(73) Assignee: Life Safety Distribution AG, Uster (CH)

( * ) Notice: Subject to any disclaimer, the term of this patent is extended or adjusted under 35 U.S.C. 154(b) by 561 days.

(21) Appl. No.: 12/356,268

(22) Filed: Jan. 20, 2009

(65) Prior Publication Data
US 2009/0188297 A1 Jul. 30, 2009

Related U.S. Application Data (60) Provisional application No. 61/023,486, filed on Jan. 25, 2008.

(51) Int. Cl.
*G01N 15/06* (2006.01)

(52) U.S. Cl.
USPC .................. 422/98; 422/83; 422/88; 422/90; 422/91; 422/92; 73/23.2; 73/23.21; 73/23.31

(58) Field of Classification Search
USPC ............... 422/83, 88, 90, 91, 92, 98; 73/23.2, 73/23.21, 23.31
See application file for complete search history.

(56) References Cited

U.S. PATENT DOCUMENTS

| | | | |
|---|---|---|---|
| 4,317,796 A | 3/1982 | Barr | 422/95 |
| 4,670,405 A * | 6/1987 | Stetter et al. | 436/151 |
| 5,217,692 A * | 6/1993 | Rump et al. | 422/98 |
| 6,026,673 A * | 2/2000 | Santini | 73/1.06 |
| 6,234,006 B1 * | 5/2001 | Sunshine et al. | 73/29.01 |
| 6,663,834 B1 | 12/2003 | Miller et al. | 422/93 |
| 2004/0215402 A1 | 10/2004 | Hsiung et al. | |
| 2006/0032745 A1 | 2/2006 | Davies et al. | |

FOREIGN PATENT DOCUMENTS

| | | |
|---|---|---|
| EP | 0 252 283 | 1/1988 |
| EP | 0 458 058 | 11/1991 |
| WO | WO 2006/111727 | 10/2006 |

OTHER PUBLICATIONS

European Search Report, dated May 13, 2009 corresponding to European application No. 09151052.9-2204.
Humidity Sensor, "HUMIREL HPC055", Technical 1 Data, Technical 2 Data, Technical 3 Data and Technical 4 Data sheets, HTS2030SMD, 4 pages, Rev. Jun. 2004.
The Sensor Company, Sensirion, Humidity & Temperature Sensor (SHT1x / SHT7x), 10 pages, Mar. 2007.

* cited by examiner

*Primary Examiner* — Brian J Sines
(74) *Attorney, Agent, or Firm* — Husch Blackwell LLP (57) ABSTRACT

A portable, relatively low power gas detector incorporates a single pellistor-type sensor for sensing an explosive gas of interest. Outputs from the sensor are corrected in accordance with ambient temperature and humidity and pre-stored correction factors based on characteristics exhibited by a plurality of similar sensors.

10 Claims, 9 Drawing Sheets

SCHEMATIC DIAGRAM OF PELLISTOR DETECTOR ELEMENT
(PRIOR ART)

*FIG. 1*

TYPICAL OPERATING CIRCUIT FOR PELLISTOR PAIR
(PRIOR ART)

TEMPERATURE AND HUMIDITY COMPENSATED SINGLE ELEMENT PELLISTOR

CROSS-REFERENCE TO RELATED APPLICATION

This application claims the benefit of the filing date of U.S. Provisional Application Ser. No. 61/023,486 filed Jan. 25, 2008 and entitled "Temperature and Humidity Compensated Single Element Pellistor". The '486 application is incorporated herein by reference.

FIELD

The invention pertains to gas sensors. More particularly, the invention pertains to calorimetric sensors of combustible atmospheric gases.

BACKGROUND

Various Calorimetric gas sensors, known as Pellistors, are commonly used in measuring combustible gases in the atmosphere. They operate by allowing flammable gas in the air to combust on the surface of a heated catalyst (typically maintained in the temperature range 350-500° C.) and measuring the excess heat generated in this exothermic reaction. The process is carried out within a flameproof housing so as not to transmit any flame to the general environment being monitored. (See, for example, 'The Pellistor Catalytic Gas Detector', E Jones, Ch. 2 in 'Solid State Gas sensors' Eds. P T Moseley and B C Tofield, Adam Hilger, 1987 and 'Calorimetric Chemical Sensors', P T Walsh & T A Jones, Ch 11 in 'Sensors Vol. 2', Eds. W Gopel, T A Jones et al, VCH, 1991).

The combustion reaction is usually promoted using a precious metal catalyst such as palladium, platinum or rhodium, which may be dispersed on a refractory support medium (e.g. alumina or zirconia) to improve its activity and longevity. Raising the temperature of the catalyst to the required working level may be achieved using a variety of heater configurations, but by far the most common is to fabricate a bead of catalyst and support material around a small wire coil which can be heated by the passage of an electric current. Typically, the bead would be roughly spherical with an overall diameter of 400-750 microns (depending on the exact design).

Figure 1:
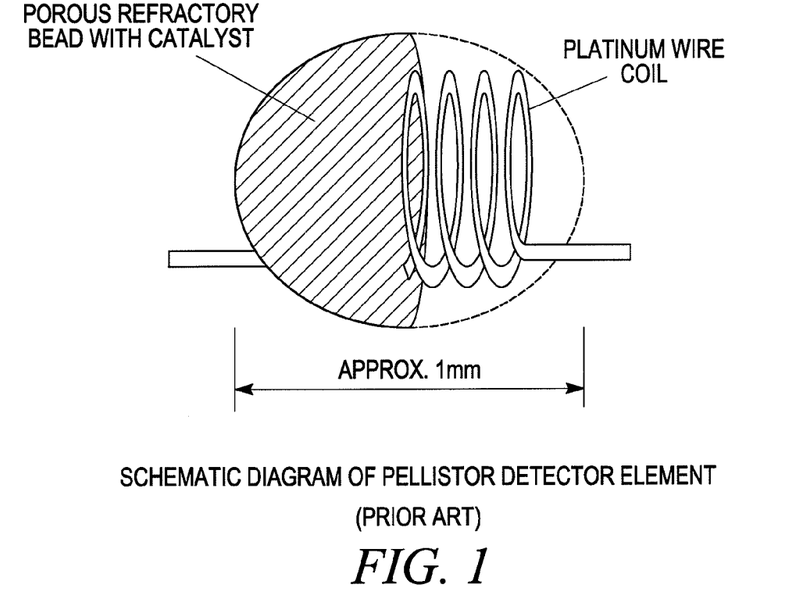
FIG. 1 is illustrates a known pellistor structure.

Although it is theoretically possible to separate the functions of heating the catalyst and measuring heat produced by the reaction (for example with a separate thermocouple or a remote IR temperature probe), it is most practical to combine these requirements in a single element. Thus, the wire coil is required to act as a resistive heater and demonstrate a significant, reproducible temperature coefficient of resistance so that the temperature increase generated by the reaction can be easily measured. The wire used is most commonly platinum, and may have a diameter of 20-50 microns. A schematic diagram of a known gas-sensitive detector, or sensor element is shown in FIG. 1.

Since the detector is essentially a thermal sensor, designed to respond to changes in temperature, it can be sensitive to numerous effects which are not caused by the combustion of flammable gas, for example:

Changes in ambient temperature;

Fluctuations in the thermal properties of the atmosphere, for example due to relative humidity or other interfering gases;

Changes in air speed which alter the cooling of the hot element;

Variations in the input power to the coil heater due to power supply instabilities.

Figure 2:
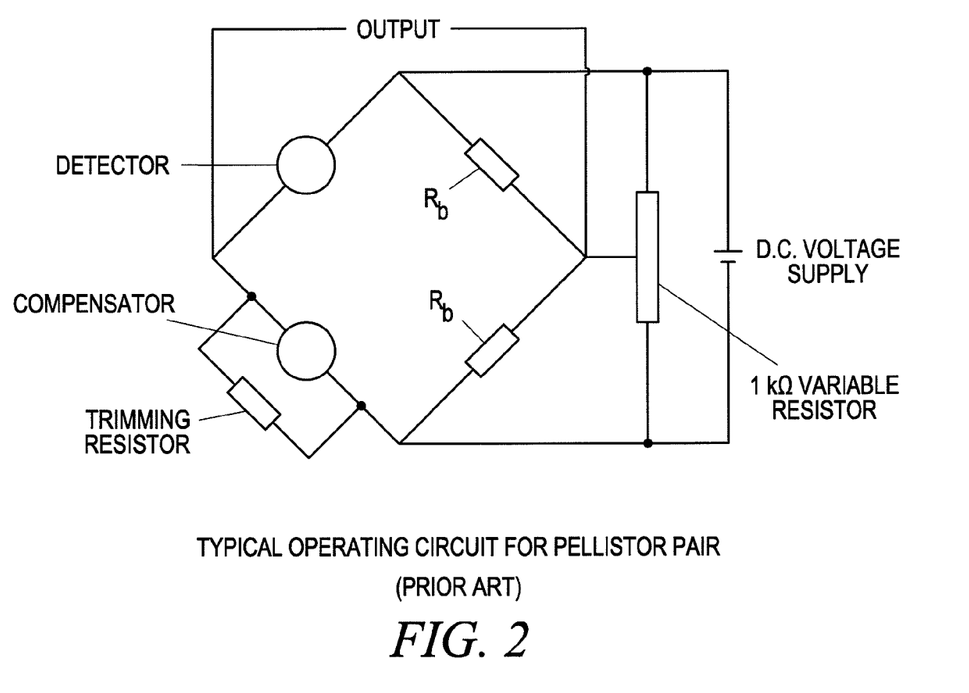
FIG. 2 illustrates known pellistor-pair compensation circuitry.

During the early development of pellistors, it was recognized that compensation for such effects was required in order to provide a practically reliable device and so it became common to deploy the detector in conjunction with a compensator element. In its simplest form, this is an identical device but without the catalyst. In some instances the bead is actually poisoned to minimize gas response. By running the detector and compensator elements in a Wheatstone bridge circuit with balancing resistors Rb as illustrated in FIG. 2, it is possible to generate an out of balance signal which substantially depends solely on the concentration of flammable species in the environment.

Such pellistor pairs have been a technical and commercial success, delivering major improvements in health and safety in many industries (e.g. mining, petrochemical processing). Improvements in bead construction, catalyst chemistry and housing design have resulted in stable, sensitive, poison-resistant products capable of operating for many years with minimal maintenance. In recent years it has become common to package the pellistor pair inside a small robust flameproof housing which can be readily incorporated into a variety of instruments or systems (e.g. 4P75, MICROpeL®75, City Technology Ltd, Portsmouth, UK).

Despite this successful background, there are still some aspects of pellistor performance where users seek improvements. Foremost of these is the power consumption—even the smallest commercial bead pairs consume in excess of 200 mW. While this is not a problem for fixed installations, in portable multi-gas responsive detectors, for example detectors which measure various different gases such as oxygen, carbon monoxide, and hydrogen sulfide using electrochemical sensors or cells, in addition to measuring an explosive gas, such as methane using a pellistor pair, the 200 mW of power consumed by the pellistor pair is a large fraction of the total instrument consumption and so limits the operational period between battery recharges.

A number of approaches to solving this problem have been tried, including:

Intermittent or cyclic operation of the detector/compensator pair so that they only run at full power for a fraction of the operating period;

Single element detector operation at different temperatures to separate the effects of interferences and flammable gases;

Single element detector operation without compensation.

The above noted methods fail to meet the stringent demands placed upon pellistors. It has been found that any method in which the detector is regularly subjected to temperature cycling tends to promote drift in the output, necessitating more frequent recalibration. In the vast majority of safety-critical applications, an uncompensated detector output is wholly incapable of meeting accuracy specifications, given the wide temperature (−40 to +55° C.) and humidity (0-100% RH) ranges over which the devices are required to operate.

However, a number of the factors which the compensator was originally designed to address have been overcome in other ways. Thus, the incorporation of elements into flameproof housings (often surrounded by porous insulators to improve shock resistance), has greatly reduced the flow rate sensitivity. Modern electronic circuits are able to provide highly reliable and accurate power supplies at relatively low cost. Therefore, the major functions of the compensator in modern designs are the correction for ambient temperature and RH as well as correction for changes in the thermal conductivity of the background atmosphere. However, this is achieved at a relatively high power consumption and significant cost (once the bead construction and pair matching are taken fully into account).

Temperature and RH changes in the environment which require compensation generally occur over a timescale which is relatively long compared with the alarm period of a pellistor ($T_{90}$ typically 30 seconds). Thus, continuous operation of the detector with intermittent compensator powering to provide periodic correction may be employed as in the MICROpeL®40 sensor (City Technology Ltd, Portsmouth, UK). This device offers up to 40% power savings when compared with conventionally operated pellistors in the same housing. However, intermittent compensator operation can be complicated to implement and requires careful (and more complex) hardware and software design to ensure correct interpretation of data. Despite the advantages offered, this approach is not acceptable to all users and so an alternative is required.

There continues to be a need for lower power pellistor based detectors of the general type described above. Preferably, lower power operation will be achievable via methodologies which do not require the types of complexities discussed above.

DETAILED DESCRIPTION

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In one aspect of the invention, conventional pellistor compensators can be eliminated. Instead, temperature and humidity sensors based on different technologies which have the required combination of adequate performance, moderate cost and very low power consumption can be used in correcting single pellistor-type sensors.

In accordance with the above, commercial integrated devices for sensing temperature and relative humidity (T/RH), including products from manufacturers such as Sensirion, (Zurich, Switzerland) and Humirel (Toulouse, France), can be used. Typically these devices consume less than 1% of the power required by a conventional coil based compensator (e.g. 0.2 mW cf>100 mW).

Using appropriate processing, mathematical correction for temperature and humidity variations in the output of a single pellistor-type sensor represents an attractive solution to the high power consumption of known compensators and offers the prospect of savings approaching 50% of current levels without the complexities generated by prior art intermittent powering schemes as described above. In addition, the processing in accordance with the invention may be usable, in combination with other developments (for example in smaller detector beads or planar heater devices), in further reducing required power consumption of such sensors.

In accordance with correcting sensor outputs, the effects on sensor performance of changes in temperature and humidity can be modeled as described subsequently.

Baseline in dry air as a function of Temperature $$_D BL_{(T)} = \frac{\left(P^{Air}_{T_{test}} - P^{Air}_{T_{cal}}\right)}{\$_{cal}} \cdot (\% \ LEL) \quad \text{(Equation 1)}$$

Baseline Change due to 0-100% nominal Relative Humidity change at temperature T $$\Delta BL_{(T)} = \frac{(P^{Air}_{wet,T_{test}} - P^{Air}_{dry,T_{test}})}{\$_{cal}} \cdot (\% \ LEL) \quad \text{(Equation 2)}$$

Methane Span Signal in dry gas as a function of temperature $$S_D CH_{4(T)} = \frac{\left(P^{CH_4}_{T_{test}} - P^{Air}_{T_{test}}\right)}{\left(P^{CH_4}_{T_{cal}} - P^{Air}_{T_{cal}}\right)} \times 100(\%) \quad \text{(Equation 3)}$$

Methane Span Signal in wet gas as a function of temperature T $$S_W CH_{4(T)} = \frac{\left(P^{CH_4}_{wet,T_{test}} - P^{Air}_{wet,T_{test}}\right)}{\left(P^{CH_4}_{dry,T_{test}} - P^{Air}_{dry,T_{test}}\right)} \times 100(\%) \quad \text{(Equation 4)}$$

Methane Sensitivity (under calibration conditions)

$$\$_{cal} = \frac{\left(P^{CH_4}_{cal} - P^{Air}_{cal}\right)}{C_{CH_4}} \cdot (mW/\% \ LEL) \quad \text{(Equation 5)}$$

Notes:

$\bar{P}^{Gas}_{test}$ = Power dissipated (mW) under the test conditions in a specific atmosphere $\bar{P}^{Gas}_{cal}$ = Power dissipated (mW) under the calibration -continued conditions in a specific atmosphere
(i.e. dry gas at 20° C. in this investigation).

$C_{CH_4}$ = Concentration of methane in air (% LEL) employed

Temperature and humidity corrections can readily be modified to take account of errors derived from the T/RH sensor output. This can be achieved by assuming that the factors are based on under/overestimates of the notional parameter variation in accordance with the manufacturers' claims (or practical data if available). Corrected readings are then scaled up/down accordingly, and the worst case result obtained by applying the values from the extremes is used to estimate overall accuracy.

The combined baseline and span deviations from the instrument calibration conditions due to changes in temperature and humidity may be expressed in terms of the gas concentration reading (% LEL) displayed by a visual display, or, monitor.

$$ID = \frac{(P^{Gas}_{test} - P^{Air}_{cal})}{\$_{cal}} \cdot (\% \ LEL) \quad \text{(Equation 6)}$$

The instrument display (ID) is a very useful way of summarizing the overall effects encountered by a user but does not resolve the individual error contributions from temperature and humidity variations. The quantitative impact of the same fundamental pellistor performance will differ in these two regimes due to the different basis of normalization used.

In an aspect of the invention, two assumptions can be used in modeling the output of a single pellistor-type sensor. First, it would be desirable to be able use a single set of correction factors for a plurality of pellistors. Mean correction factors can be established across a batch or plurality of pellistors or sensors. These factors can then be applied to the raw data from the individual sensors to determine the overall effect and to implement the desired correction. As manufacturing techniques improve and increase the reproducibility of pellistor performance on a unit-to-unit basis, use of a single correction factor, or factors, across a wide population becomes even more effective.

Secondly, it is useful to assume that the temperature and humidity readings provided by the T/RH sensor correspond to sensor limits of performance, based on data sheet specifications, as provided by the manufacturers thereof. In another aspect of the invention, not only is it important to take into account the variability of the pellistor elements, it is also desirable to take into account errors derived from the temperature and RH measurements.

The projected impact on instrument baseline and span performance was initially established using data acquired from a set of 8 MICROpeL®40 pellistors (Batch 1). These were employed as they provide a convenient means to independently control the detector and compensator elements to a desired constant temperature and thereby undertake comparisons of uncompensated and compensated performance under nominally identical environmental conditions. The normal operating points are defined by the temperature achieved by the element when subjected to a voltage of $V_d$=1.75V (detector) and $V_c$=1.30V (compensator). As would be understood by those of skill in the art, a control circuit could be used to operate either the detector alone or both the detector and compensator at the normal operating points, depending on the type of measurement required.

Sensor output can be defined as either the difference in power dissipation between the detector and compensator elements for paired (compensator+detector) operation or as the power dissipated by the detector for single bead (detector only) operation. Measurement and recording of sensor outputs can be carried out via an exemplary automated data acquisition system based around a PC running a bespoke Labview application combined with a Keithley 2000 Digital Multimeter and 7001 Multiplexer.

The sensors were mounted in an environmental chamber allowing tests over a range of ambient temperatures (−20° C. to +55° C.) under wet and dry conditions. The control circuitry was maintained at ambient temperature to minimize any impact upon sensor performance. Test gases were supplied by BOC; 2.5% methane in air (Alpha-Standard grade, concentration tolerance ±1%) and BTCA certified grade air. Gases saturated with water vapor at a specific test temperature were obtained by passing dry cylinder gases through a single Dreschel bottle within the chamber. A constant flow rate of 1000 cc/min was employed throughout.

After allowing the elements to stabilize for a minimum of 16 hours (i.e. overnight) they were calibrated in the respective dry primary test gas at 20(±)° C. in both single bead or paired operation. Baselines were taken as the sensor output in air and methane span signals as the difference between the sensor output in the target gas and in air. In all instances, a 10-minute exposure time was employed to ensure that the air and gas responses had attained a steady state before being recorded.

On the basis of the mean performance of the batch under various conditions, corrections for zero (simple offset in % LEL $CH_4$ terms) and methane sensitivity (span multiplier) were calculated for 5 temperature and RH combinations encompassing the extremes of the operating environmental range. Errors of 2° C. and 5% RH in the measurements of the ambient conditions by the T/RH sensor were also assumed, in accordance with the worst case scenario in the manufacturer's data sheet (series SHT1x/SHT7x Humidity & Temperature sensor, Sensirion, Zurich, Switzerland). The batch mean correction (learning set) was then applied to raw data from each sensor in turn and the spread of performance so determined was plotted. Thus, the performance of paired pellistor pairs was compared with the modeled performance of detector elements corrected using 'worst case' estimates of the temperature and RH. Subsequently, the calculations were repeated using mean correction factors determined from a second learning set of 8 notionally similar sensors (Batch 2).

Figure 3:
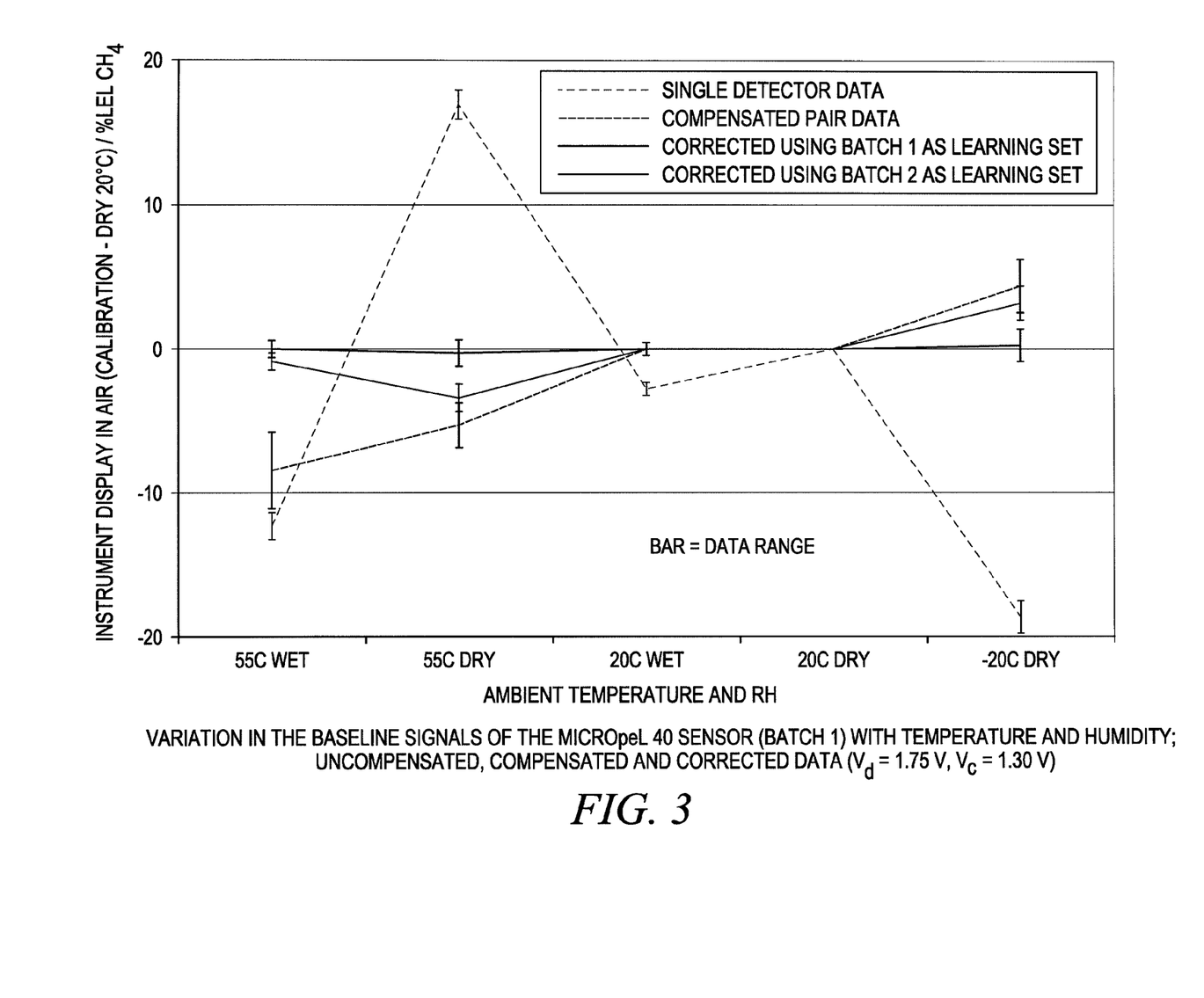
FIG. 3 is a graph which illustrates baseline compensated, uncompensated and corrected exemplary pellistor outputs in air as a function of temperature and humidity.
Figure 4:
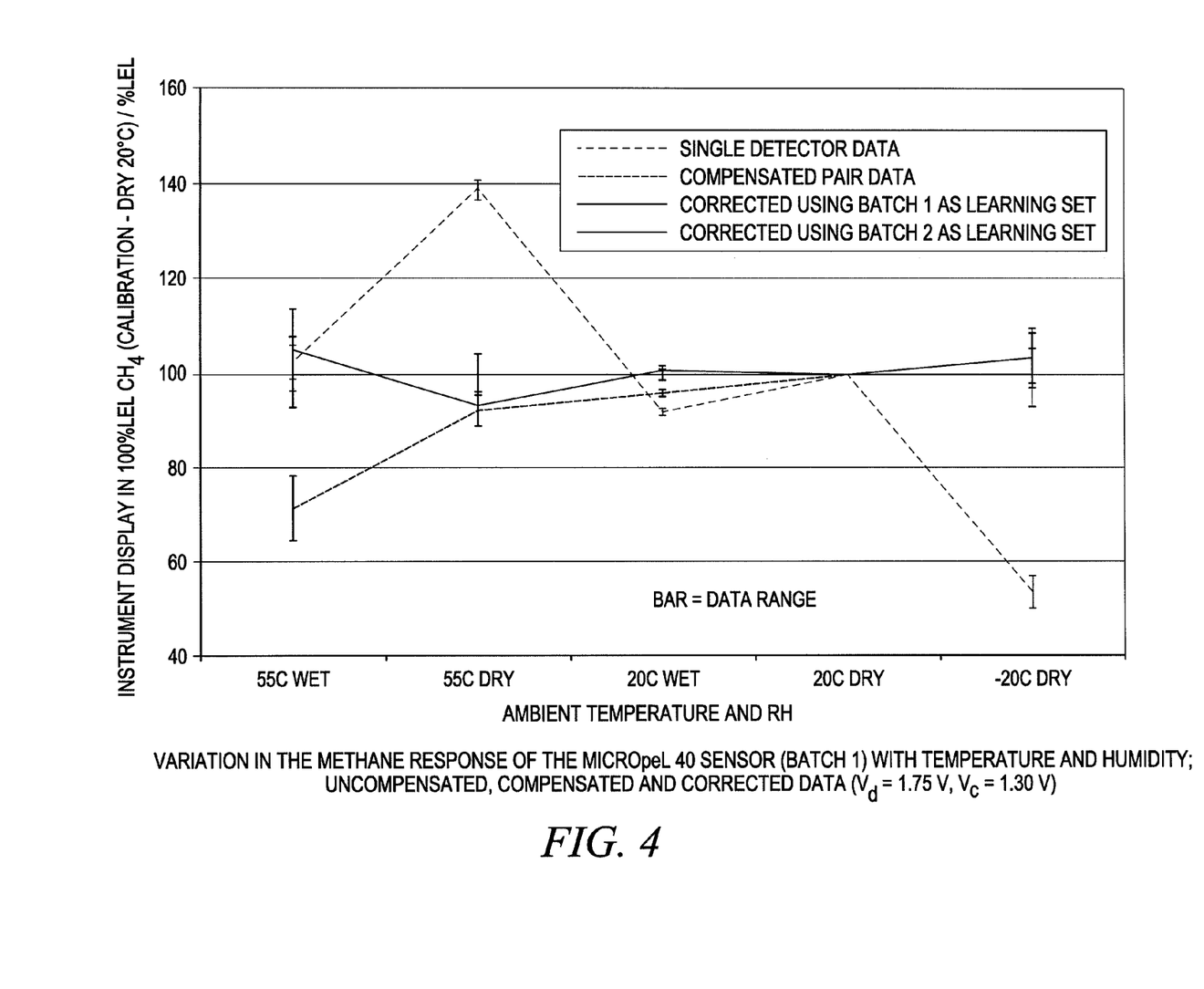
FIG. 4 is a graph which illustrates compensated, uncompensated and corrected exemplary pellistor responses to methane as a function of temperature and humidity.

The graphs of FIG. 3 (baseline effect) and FIG. 4 (methane sensitivity effect) illustrate estimates of the final instrument output which would be observed under the various operating and environmental conditions. As illustrated, single element performance was much worse than that from the paired devices, as expected. However, it is also clear that single element data can be corrected by the above described method and is comparable with, or better than that obtained in paired operation. Furthermore, there is not a large difference between the performance achieved when using compensation factors determined from two different batches of MICROpeL®40 sensors.

The results noted above show that achievable levels of precision in practical T/RH sensor performance, in accordance with the second above noted assumption, could deliver adequate performance.

Further tests carried out on three additional sets of similar sensors (Batches 3, 4 and 5) confirm this result and more conclusively demonstrate the applicability of the present method across different sensor batches. These batches included eight, seven and seven MICROpeL®40 sensors respectively.

In accordance with the approach discussed above, batch 3 was used as the learning set and used to calculate generic correction factors for baseline and methane span at each of the measuring points. These values were then applied to the individual sensor results from batches 4 and 5, generating the graphs shown in FIGS. 5, 6, 7 & 8. Here the baseline and span variations have been further resolved in terms of temperature and humidity effects, which explains the generally smaller shifts observed from the calibration conditions than in FIGS. 3 and 4. The raw, uncorrected pellistor outputs indicate that all five pellistor batches exhibit very similar behavior.

Figure 5:
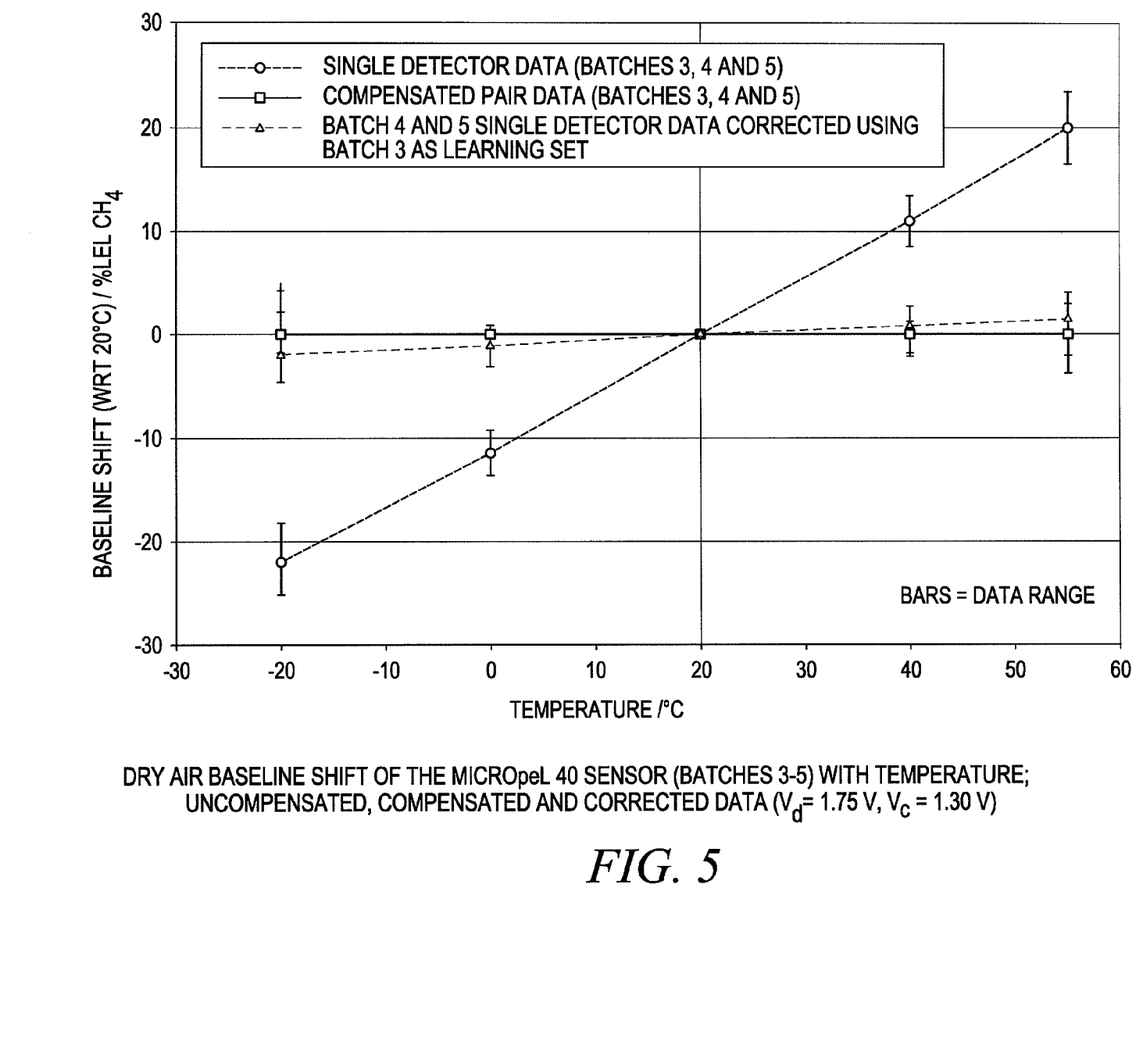
FIG. 5 is a graph which illustrates dry air baseline shift for compensated, uncompensated and corrected exemplary pellistor outputs as a function of temperature.

FIG. 5 illustrates air baseline data from batches 3, 4 & 5 for single detector and paired operation as a function of temperature. The performance of the single bead was typically 4-5 times worse than that of the pairs, which show shifts of less than ±5% LEL $CH_4$ equivalent relative to the 20° C. value. FIG. 5 also illustrates the single detector data from batches 4 and 5 corrected using generic factors obtained by analysis of the behavior of batch 3. Once the spread of data is taken into account, it can be seen that the corrected single bead performance approaches that obtained from pairs of beads.

Figure 6:
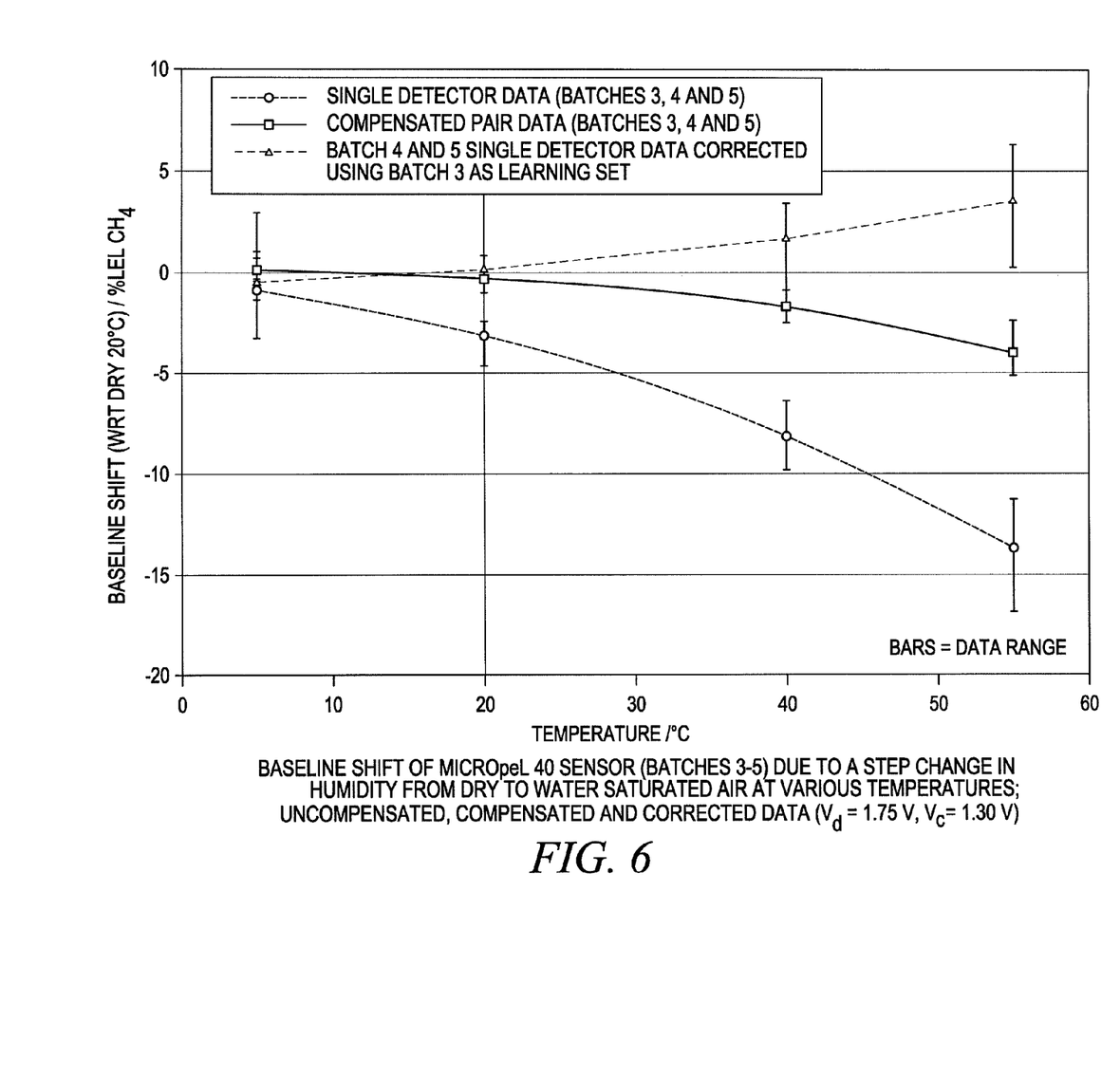
FIG. 6 is a graph which illustrates baseline shift in air for compensated, uncompensated and corrected pellistor outputs in response to a step change in humidity as a function of temperature.

The effect of saturating the air stream with water also had a marked influence on single detector baselines, with a much smaller impact upon pairs as shown in FIG. 6. The shift from true zero baselines increases at higher temperatures, with maximum errors at 55° C. of ca. −17% LEL $CH_4$ and −5% LEL $CH_4$ (cf. dry 20° C. conditions) respectively. In this case, the corrected single bead performance showed similar offsets to the pairs, but with opposite polarity.

Figure 7:
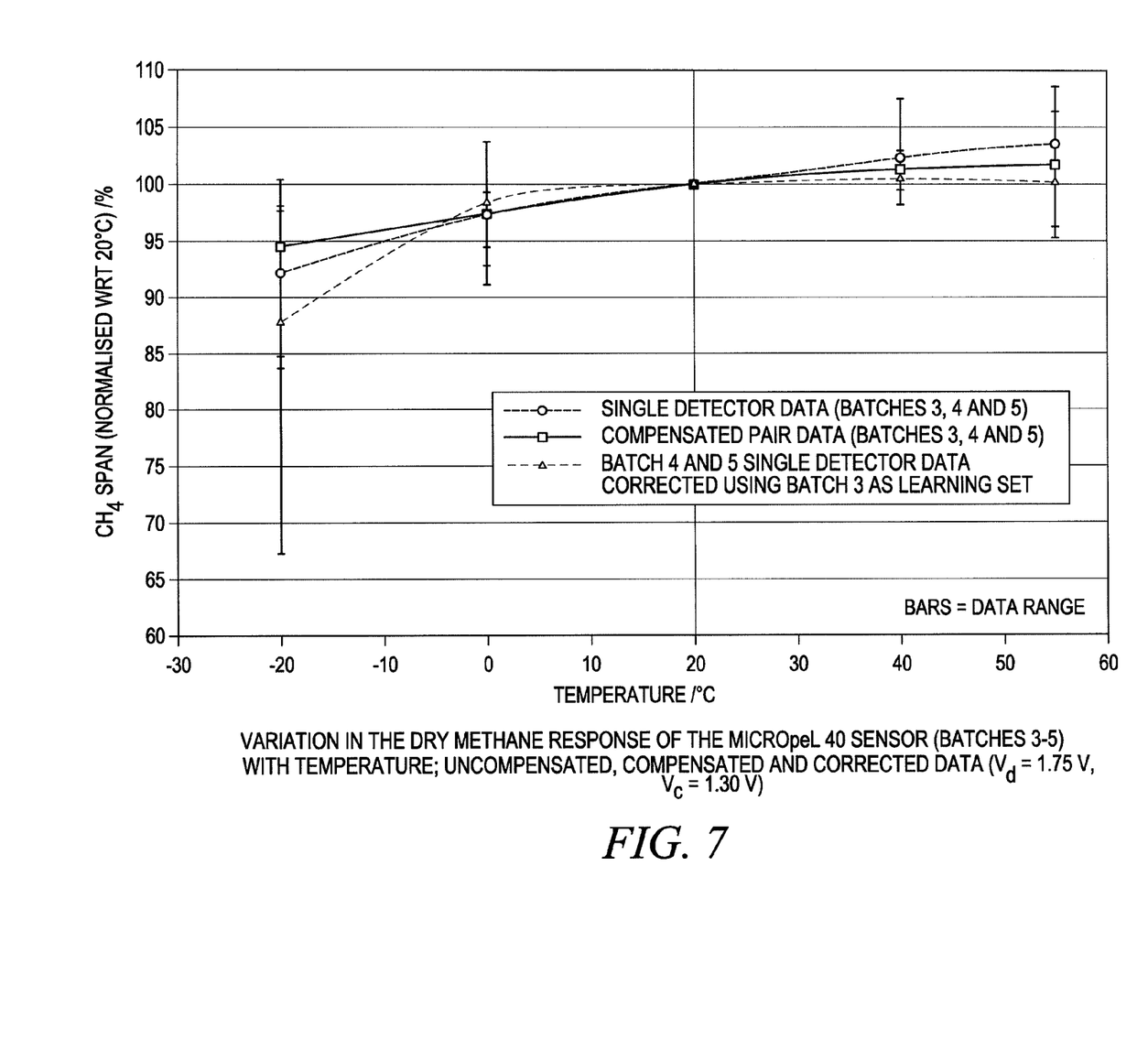
FIG. 7 is a graph which illustrates variation in dry methane response for compensated, uncompensated and corrected exemplary pellistor outputs in response to variations in temperature.
Figure 8:
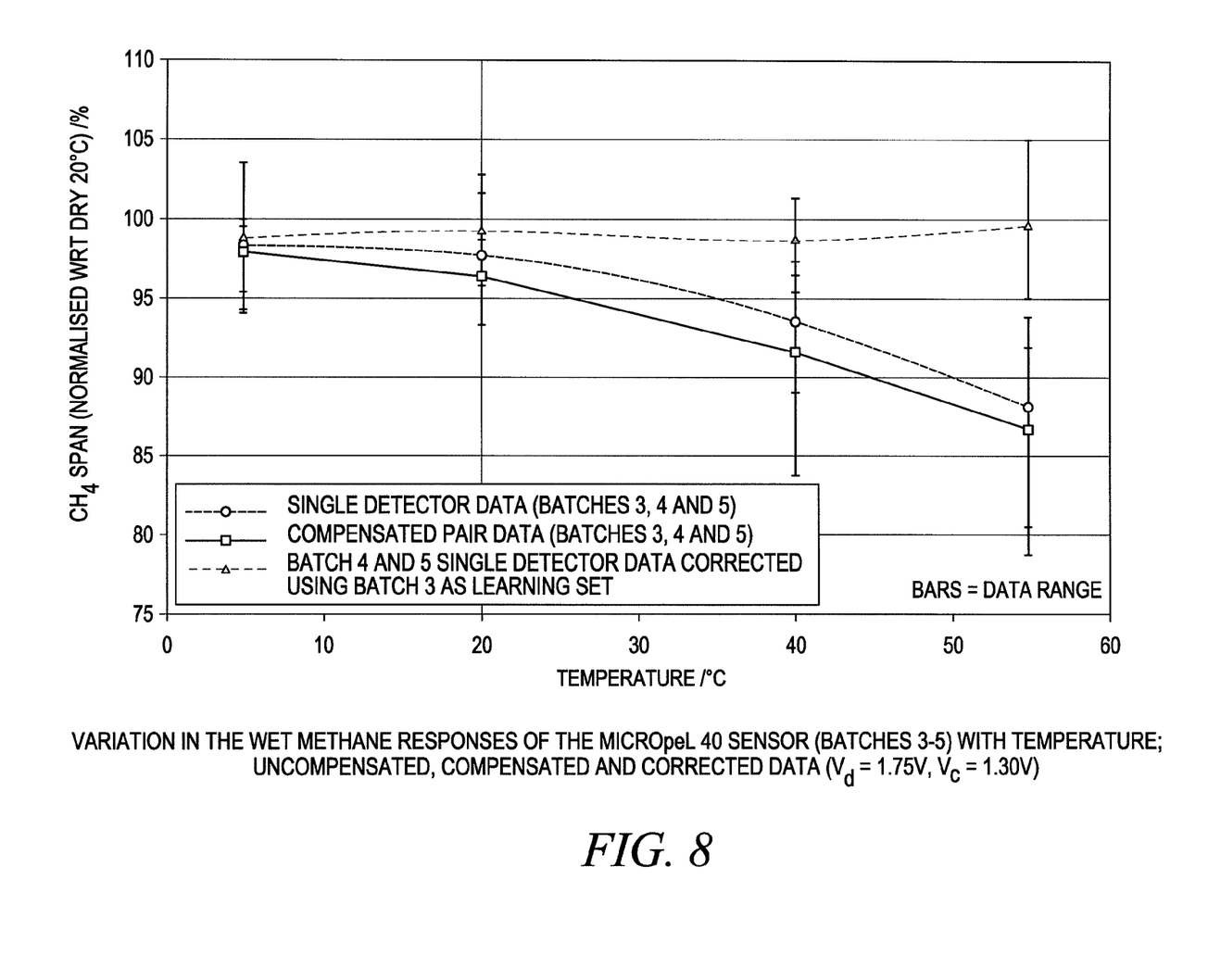
FIG. 8 is a graph which illustrates variation in wet methane response for compensated, uncompensated and corrected exemplary pellistor outputs in response to variations in temperature.

FIGS. 7 and 8 illustrate the impact of temperature and humidity shifts on the span behavior of the same devices. Single bead and paired behavior show much smaller differences than is the case when comparing baselines. However, with the exception of the −20° C. data, FIG. 7 (which is largely attributed to 1 or 2 outlying results), it is again clear that the corrected single bead performance is generally superior, especially when considering the humidity shifts.

This data shows that the consistent performance of single beads within and between sensor batches allows deviations caused by temperature & humidity variations to be adequately corrected using mean data from the batch. The same generic correction factors, when applied to sensors other than the learning set, still give adequate baseline and gas response correction. The overall performance of externally corrected single elements is generally equal to, and in some cases exceeds that of traditional pellistor pairs.

It is therefore apparent that a viable alternative to the use of an expensive, high power consumption pellistor compensator exists, which will offer significant advantages in many applications. Although the examples have been based on constant temperature operated single elements, the same techniques may be applied to pellistors operated in different configurations, such as constant voltage drive, or, constant current drive, with appropriate correction factors. However, constant temperature operation is generally preferred. Maintaining the detector catalyst at its optimum operating temperature tends to minimize variations between sensors and provide more stable output.

Hence, in accordance with the invention, temperature and humidity-compensated outputs can be produced from a single pellistor-type sensor using one or more of, generic span and baseline compensation factors, not values which are specific to a particular device, independent of measured temperature and RH data. Those of skill in the art will of course recognize that one could apply correction factors based on a pre-calibration of every sensor. However, commercially, the use of generic methods across populations can be expected to be much more cost effective.

Figure 9:
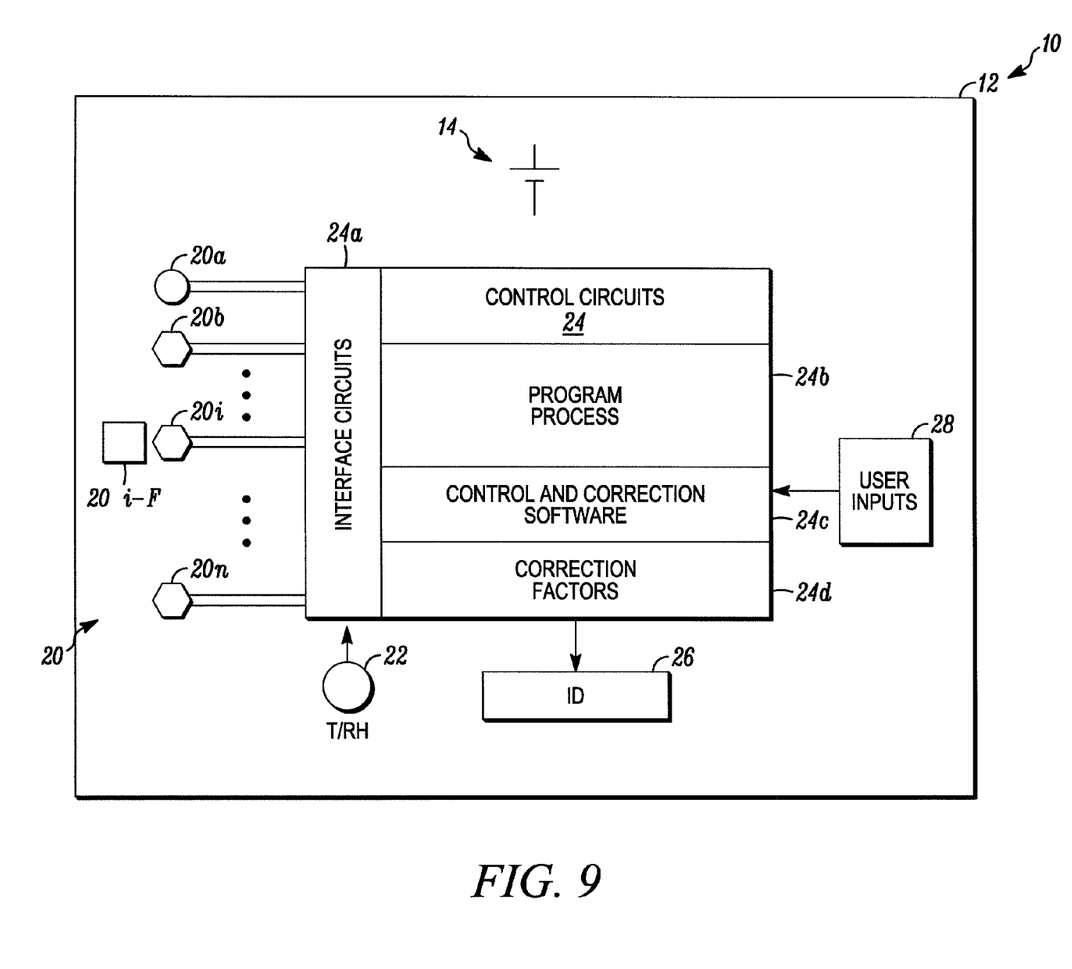
FIG. 9 is a block diagram of a multi-gas portable detector which embodies the invention.

FIG. 9 illustrates a block diagram of an exemplary, portable multi-gas detector 10 which embodies the invention. One gas could be a selected explosive gas of interest. Other gases could include oxygen, carbon monoxide or hydrogen sulfide for example. Detector 10 advantageously benefits from lower power consumption, in accordance with the above described correction method by using only one pellistor to sense the explosive gas with outputs therefrom being corrected as described above, and not compensated using a second pellistor.

Detector 10 includes a housing 12 which carries a rechargeable battery 14 which functions as a power source for the unit. A plurality of sensors 20, responsive to selected gases of interest, are carried by housing 12 so as to be exposed to ambient atmosphere as would be understood by those of skill in the art. Each of the sensors 20i could be protected by airborn contaminants by one or more filters such as 20i-F.

Sensor 20a could be implemented with a single pellistor which would respond to a selected, ambient explosive gas. A compensating pellistor is not needed in the detector 10. Remaining sensors 20b . . . 20n could be implemented with other selected technologies, without limitation. For example, they could be implemented using electrochemical cells.

Detector 10 also includes a non-catalytic sensor of temperature and humidity (T/RH) 22 also exposed to the ambient atmosphere. Those of skill in the art will also recognize that the location of sensor 22 in detector 10 would take into account heat given off by pellistor 20a. Preferably any thermal cross-talk between pellistor 20a and sensor 22 would be minimized.

Housing 12 carries control circuits 24 which include interface circuitry 24a coupled to the pellistor 20a, electrochemical sensors 20b . . . 20n and sensor 22. Signals received by interface 24a are coupled, after processing as would be appropriate, to programmable processor 24b which executes pre-stored control and correction software 24c. Pre-stored correction factors 24d, established based on previous measurements of pluralities of other pellistors, as described above, are used by the correction software 24c in processing and correcting outputs from pellistor 20a. It will be understood that the software 24c and correction factors 24d are stored on computer readable storage units such as semiconductor, magnetic or optical storage units all without limitation.

Detector 10 also carries an instrument display (ID) such as 26 and operator input elements 28 such as switches, keyboard and the like all without limitation. Display 26 can provide feedback to the user as to concentrations of gases selected by the user via interface, operator inputs 28. Advantageously, since pellistor 20a does not need an associated compensating pellistor, power consumption required for the detector 10 is substantially less than required using a compensated pellistor pair, as illustrated in FIG. 2 hereof. If desired, detector 10 could include additional pellistors which could respond to other explosive gases with outputs corrected in accordance with the above described method.

Figure 10:
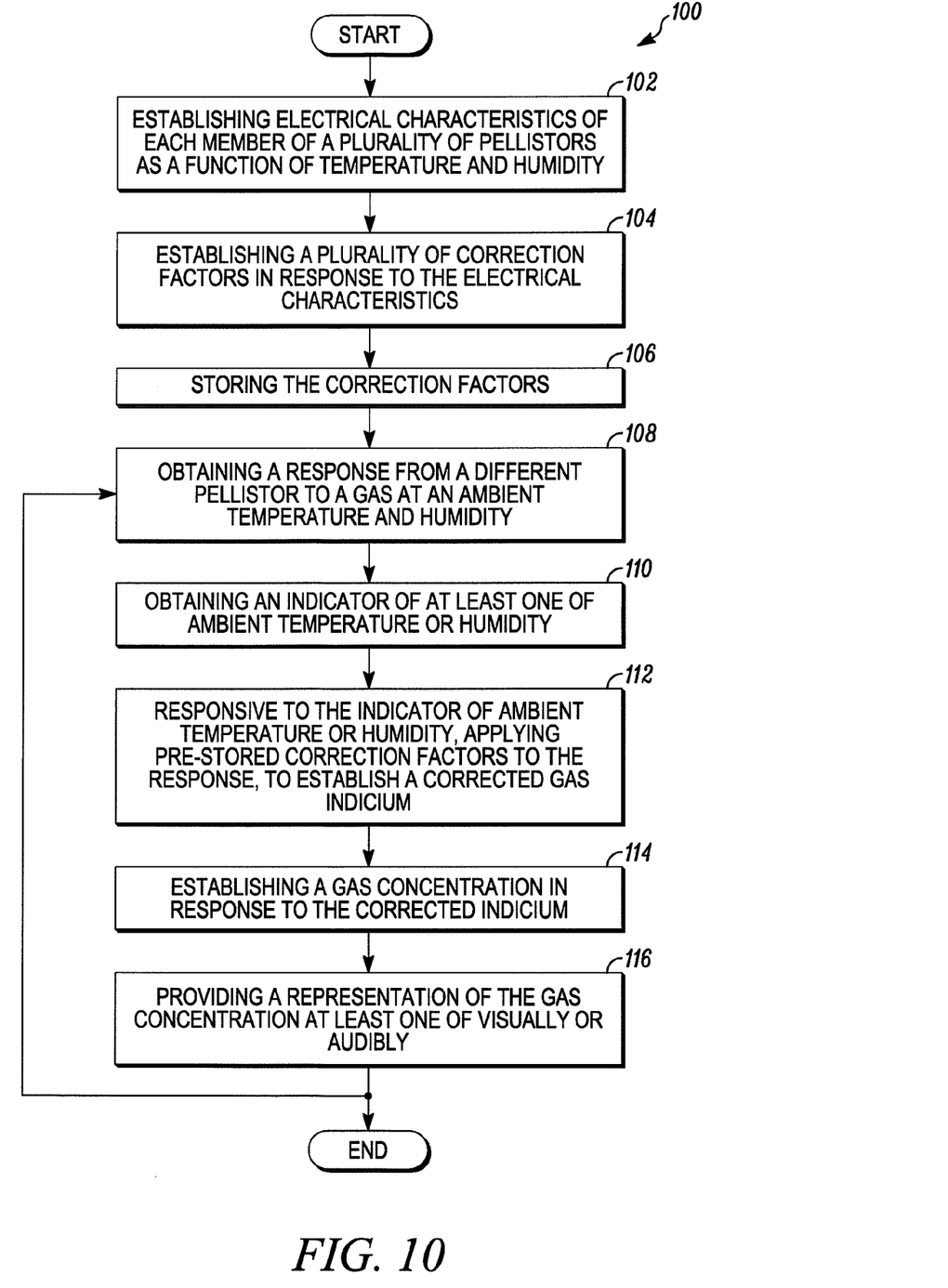
FIG. 10 is a flow diagram of a method in accordance with the invention.

FIG. 10 is a flow diagram of a method 100 which embodies the invention. Initially, as at 102, characteristics of each member of a plurality of pellistors are established as a function of temperature and humidity. A plurality of correction factors are established, as at 104, in response to evaluating the established characteristics. The correction factors are stored as at 106.

A response to a specific gas at an ambient temperature and humidity is subsequently obtained from a pellistor, not a member of the plurality of pellistors as at 108. An indicator of ambient temperature and/or humidity can be obtained as at 110.

Responsive to the current ambient temperature and/or humidity, correction factors can then be applied to that response, for that gas, at the current temperature and humidity as at 112. A gas concentration, as a percent of lowest explosive level, can be established for that gas at that temperature and humidity, as at 114. That percentage can be displayed, or an audio concentration indication can be emitted as at 116. The establishment of gas concentrations can be repeated as at 108-116 as needed using the sensed ambient conditions and the pre-stored correction factors.

From the foregoing, it will be observed that numerous variations and modifications may be effected without departing from the spirit and scope of the invention. It is to be understood that no limitation with respect to the specific methods discussed, or, apparatus illustrated herein is intended or should be inferred. It is, of course, intended to cover by the appended claims all such modifications as fall within the scope of the claims.

The invention claimed is:

1. A detector comprising:
   a plurality of catalytic sensors;
   a plurality of correction factors where each correction factor of the plurality of correction factors is a mean of the respective correction factors of the plurality of catalytic sensors determined at a selected value of one of temperature and humidity and where the plurality of correction factors are determined across an operating range of the plurality of catalytic sensors at respective selected values of the one of temperature and humidity;
   at least a first catalytic sensor from the plurality of catalytic sensors;
   the at least first catalytic sensor of the plurality of catalytic sensors implemented with only a single pellistor to sense a first explosive, ambient, gas;
   a non-catalytic sensor of at least one of ambient temperature and ambient humidity; and
   control circuits coupled to the single pellistor with the control circuits including pre-stored values of the plurality of correction factors, the control circuits retrieving at least one of the pre-stored correction factors using a measured value of at least one of temperature and humidity from the non-catalytic sensor with the at least one retrieved pre-stored correction factor combinable with gas indicating indicia from the single pellistor to produce corrected gas indicating indicia, absent data from a compensating pellistor.

2. A detector as in claim 1 which includes combining at least one output from the non-catalytic sensor with the correction factors and the gas indicating indicia.

3. A detector as in claim 2 which includes at least a second, different gas sensor, responsive to a second different ambient gas, coupled to the control circuits.

4. A detector as in claim 3 which includes a user selected gas specifying input coupled to the control circuits, and where the control circuits produce gas indicating indicia responsive to a user selected gas.

5. A detector as in claim 2 where the control circuits include a binary element wherein the correction factors are stored.

6. A detector as in claim 5 where the control circuits include binary processing circuits which process the stored correction factors and the gas indicating indicia from the first catalytic sensor.

7. A detector as in claim 6 which includes the non-catalytic sensor with an output coupled to the binary processing circuits.

8. A detector as in claim 7 wherein the binary processing circuits select at least one pre-stored correction factor in response to an output from the non-catalytic sensor.

9. A detector as in claim 8 which includes an output device coupled to the binary processing circuits for presenting at least one of a visual or an audible indicator as to concentration of the first gas.

10. A detector as in claim 9 which includes additionally, a plurality of electrochemical gas sensors, responsive to different gases, coupled to the control circuits and where the control circuits extract a respective correction factor, for the catalytic sensor, from the binary element in response to at least sensed temperature.

\* \* \* \* \*